United States Patent
Keenan et al.

(10) Patent No.: US 8,247,616 B1
(45) Date of Patent: Aug. 21, 2012

(54) METHOD FOR THE DECOMPOSITION OF CUMENE HYDROPEROXIDE

(75) Inventors: Scott R. Keenan, Marlton, NJ (US); Michael K. Hagans, Wheelersburg, OH (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 13/432,141

(22) Filed: Mar. 28, 2012

Related U.S. Application Data

(63) Continuation of application No. 12/797,321, filed on Jun. 9, 2010, now abandoned.

(51) Int. Cl.
 *C07C 45/53* (2006.01)
 *C07C 37/08* (2006.01)
 *C07C 2/86* (2006.01)

(52) U.S. Cl. .......... 568/385; 568/798; 585/323

(58) Field of Classification Search ............ 568/385, 568/798; 585/323
See application file for complete search history.

(56) References Cited

U.S. PATENT DOCUMENTS

| | | |
|---|---|---|
| 4,358,618 A | 11/1982 | Sifniades et al. |
| 5,254,751 A | 10/1993 | Zakoshansky |
| 5,371,305 A | 12/1994 | Hood |
| 5,430,200 A | 7/1995 | Hood |
| 5,463,136 A | 10/1995 | Blackbourn et al. |
| 5,998,677 A | 12/1999 | Yasaka et al. |
| 6,057,483 A | 5/2000 | Zakoshansky et al. |
| 6,201,157 B1 | 3/2001 | Keenan |
| 6,225,513 B1 | 5/2001 | Zakoshansky et al. |
| 6,307,112 B1 | 10/2001 | Weber et al. |
| 7,109,385 B2 | 9/2006 | Tatake et al. |
| 7,166,752 B2 | 1/2007 | Marshall et al. |
| 7,482,493 B2 | 1/2009 | Nelson et al. |

OTHER PUBLICATIONS

The International Search Report mailed Feb. 17, 2012 in International Application No. PCT/US2011/039068.

*Primary Examiner* — Sikarl Witherspoon
(74) *Attorney, Agent, or Firm* — Faegre Baker Daniels LLP

(57) ABSTRACT

A method of producing phenol, acetone and alpha-methyl styrene. A mixture of cumene hydroperoxide and dimethylbenzyl alcohol is provided. The mixture is subjected to a first stage reaction in the presence of about 0.5 to 1.5 wt. % water and about 20 to 400 ppm sulfuric acid at a reactor pressure of about 450 to 760 mm Hg, a temperature of about 60 to 85° C., and a residence time of 4 to 45 minutes to produce a composition having an acetone to phenol mole ratio of about 1 to 1.5. The composition is subjected to a second stage reaction in the presence of about 0.5 to 3 wt. % additional water with a second stage reactor temperature of about 110 to 150° C. and a residence time of 0.5 to 30 minutes.

10 Claims, 1 Drawing Sheet

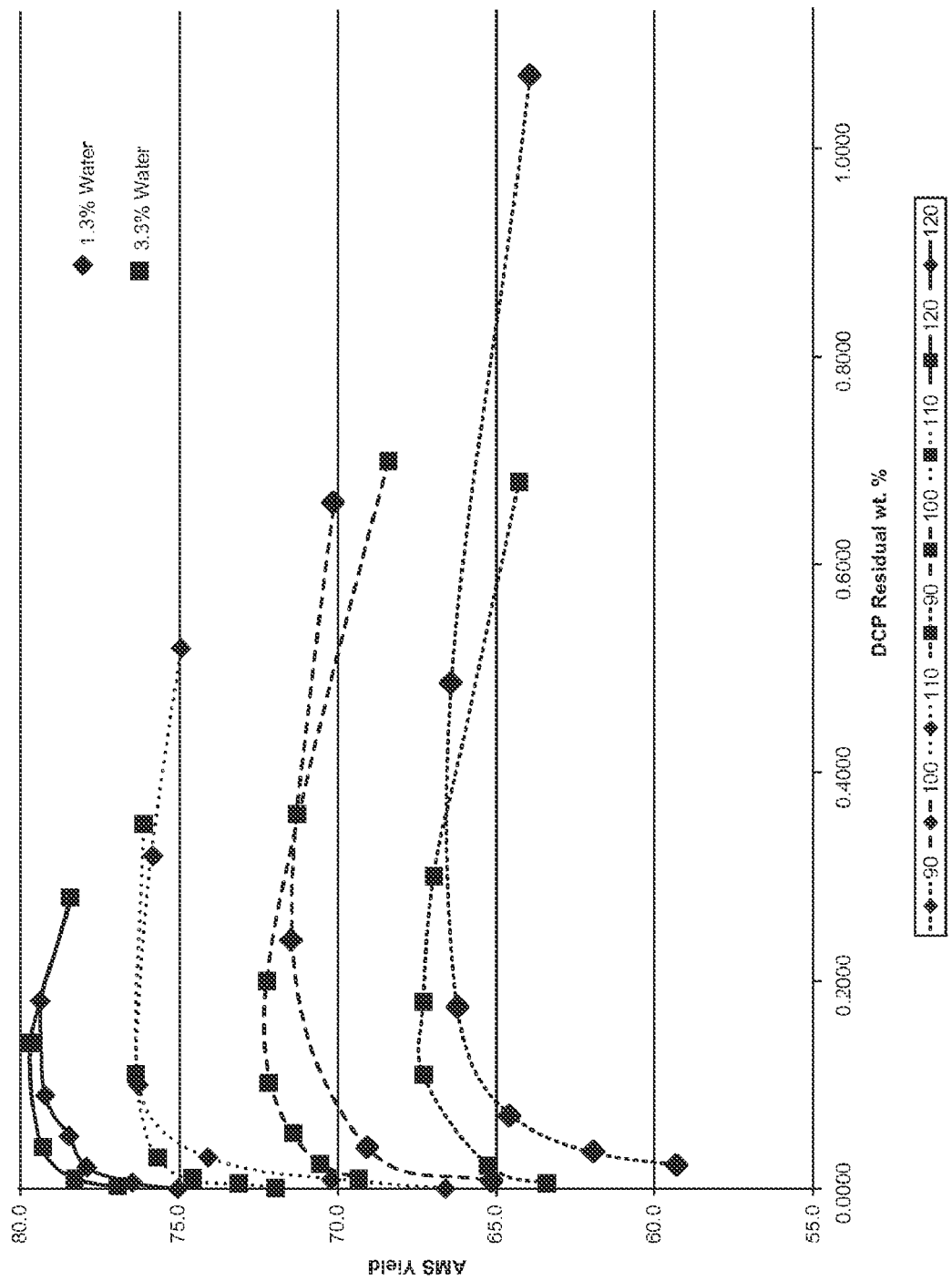

METHOD FOR THE DECOMPOSITION OF CUMENE HYDROPEROXIDE

CROSS-REFERENCE TO RELATED APPLICATIONS

This application is a continuation of U.S. patent application Ser. No. 12/797,321, filed Jun. 9, 2010, which is incorporated by reference in its entirety.

FIELD OF THE INVENTION

The present invention relates to an improved method for the production of phenol, acetone and alpha-methyl styrene (AMS) from a cumene hydroperoxide and dimethylbenzyl alcohol (DMBA) mixture.

DESCRIPTION OF RELATED ART

The dominant method for producing phenol and acetone is via air oxidation of cumene to cumene hydroperoxide (CHP), followed by acid catalyzed decomposition of the CHP selectively to phenol and acetone. Dimethylbenzyl alcohol (DMBA) is formed as the principal side product in the oxidation step, and is subsequently dehydrated to alpha-methyl styrene (AMS) in the same acid catalyzed decomposition step.

The acid catalyzed decomposition of CHP is well known, most modern processes utilizing a two step, continuous flow approach to optimize overall yield in this step, especially of DMBA to AMS. Examples of such prior art are U.S. Pat. Nos. 7,482,493, 7,109,385, 6,307,112, 6,225,513, 6,201,157, 6,057,483, 5,998,677, 5,463,136, 5,430,200, 5,371,305, and 5,254,751, all of which are hereby incorporated by reference. These and other derivative approaches are based on the work of S. Sifniades et. al. as detailed in U.S. Pat. No. 4,358,618, which is also hereby incorporated by reference.

A key to the two stage approach is to use a lower temperature first stage, targeting the selective decomposition of CHP into phenol and acetone while maximizing preservation of DMBA (and ultimately the AMS product from it) as dicumyl peroxide (DCP). The second stage is typically run shorter and hotter to selectively decompose the DCP into phenol, acetone and AMS, and dehydrate the residual DMBA from the first stage to AMS.

A variety of improvements have been demonstrated by changing the conditions of the CHP decomposition, essentially through dilution with acetone, water, phenol or cumene, separately or in various combinations, though some improvements focus on the equipment, such as the use of multitudinous reaction stages. Zakoshansky et. al. references and summarizes these various approaches in U.S. Pat. No. 5,254,751, including one of the more innovative approaches where the acid is partially neutralized with amines prior to the second stage.

All of these approaches have plusses and minuses, typically requiring recycling of significant amounts of product material back to this part of the process, higher levels of acid catalyst (thus requiring more base to neutralize the reaction product prior to distillation) and/or additional complexity in both equipment count and control, for what in most cases is a marginal gain in selectivity over commonly practiced optimized approaches. Many approaches do not consider potential detrimental downstream impacts in terms of yield, energy, product quality and equipment count/complexity.

It has been found that adding only water, an additional 0.5 to 5 wt. %, just to the feed of the second stage, allows the temperature in the second stage to be fixed in a much narrower, more optimal range, independent of overall process rate. However, since DMBA, water and AMS are in equilibrium in the second stage, it was expected that the DMBA concentrations would be significantly higher at the same optimum DCP range, resulting in a slight yield penalty. Adding water to the feed of the second stage did significantly increase the maximum DMBA and DCP to AMS yield obtainable; however, it was surprising to find this optimum at essentially the same DMBA residual and a much lower DCP residual. The much lower DCP residual in particular has yield and product quality implications in the purification part of the process.

SUMMARY OF THE INVENTION

The present invention relates to a method for the production of phenol, acetone, and alpha-methyl styrene from a mixture of cumene hydroperoxide and dimethylbenzyl alcohol wherein the first stage is carried out with an acetone to phenol mole ratio of 1.0-1.5, water content of 0.5 to 1.5 wt. %, sulfuric acid concentration of 20-400 ppm, a reactor pressure of 500-760 mmHg, and a temperature of 60-85° C., being optimized to maximize the yield of dicumyl peroxide from cumene hydroperoxide and dimethylbenzyl alcohol under any specific set of feed and operational conditions. Additional water, 0.5 to 5 wt. %, is then added prior to the second stage which is maintained preferably at 130-140° C., regardless of residence time by controlling the rate of water addition. Water addition at a fixed temperature is then further refined to minimize residual dicumyl peroxide and maximize overall dimethylbenzyl alcohol to alpha-methyl styrene yield.

BRIEF DESCRIPTION OF THE DRAWINGS

FIG. 1 is a graph of AMS yield and second stage residual DCP versus 10 temperature, with and without approximately 2% additional water added.

DETAILED DESCRIPTION

In accordance with the present invention, the decomposition process, especially the second stage, is run at higher temperatures, e.g., 110-150° C., most preferably in the range of 130-140° C., and shorter times to balance maximum yield against the rate of organic fouling and the thermal decomposition of DCP, so as to give additional DMBA equivalents. Yield is optimized in the second stage by monitoring residual DCP and DMBA and targeting levels that have been established as representing optimum yield at a given feed composition to, and operation of, the first stage. However, most processes have fixed equipment in the decomposer second stage in terms of residence time, and so at slower overall process rates, or with other changes in the process ahead of the decomposition stage, the temperature should be decreased in the second stage of decomposition, which inherently will adversely affect AMS from DMBA yield. Even if one is at the proper DCP and DMBA levels for that particular temperature, that optimum is inferior to those at higher temperatures and the optimum residual DCP level is higher (see FIG. 1), which can affect yield and product quality downstream of decomposition.

In an embodiment of the present invention, a method for the production of phenol, acetone and alpha-methyl styrene from a mixture of cumene hydroperoxide and dimethylbenzyl alcohol is described wherein the first stage is carried out with an acetone to phenol mole ratio of about 1.2-1.5, a water content of about 1.0-1.5 wt. %, sulfuric acid concentration of about 300-350 ppm, a reactor pressure of about 500-600 mm Hg, a temperature of about 75-81° C., and a 5-6 minute residence time, mixing being provided via vigorous boiling of the mixture and return of the subsequently condensed volatiles. Additional water, about 1-2% was added to the product mixture obtained under the aforementioned conditions, and the resulting material fed to a plug flow reactor operating at 125-135° C., the temperature being adjusted as high as possible such that 0.16-0.22 wt. % DMBA and 0.01-0.03 wt. % DCP were realized in the second stage product effluent. The detailed data described in Example 1 below yielded FIG. 1, and the concept was validated in a commercial unit as described in the subsequent Examples, showing the improvement in yield maximum versus residual DCP to lower DCP levels, and the yield benefit of both higher temperature use and additional water added to the second stage feed.

EXAMPLES

Example 1

The results in FIG. 1 were generated using a well stirred glass reactor that was charged with 15 ml of a solution of 1/1 molar phenol/acetone spiked with approximately 8.2% DCP, 1.3% DMBA, 1.4% AMS, 12% cumene, and sufficient water added to give either 1.3% or 3.3% water content. The solution was brought to target temperature, and 8 µL of 0.5 molar sulfuric acid added (approximately 25 ppm in the bulk reaction) to start the reaction. Samples were taken at various times, neutralized with a small amount of base, and analyzed for a complete component profile.

Example 2

A CRP-containing stream with 80% CRP, 3.6% DMBA, 0.4% acetophenone (AP), and the residual cumene, was fed to the back mixed first stage of a commercial CRP decomposer operating under conditions of vigorous boiling at 550-600 mm Hg pressure, 78-80° C., a 1.25-1.35 mole ratio of acetone to CRP, 5-6 minute residence time, 300-350 ppm of sulfuric acid, and 1.0-1.3 wt. % water under optimum conditions. With no additional water added ahead of a plug flow second stage with 0.8-1.0 minutes of residence time, an average AMS yield of 80.8% was obtained at 108 C, with 0.09 to 0.12 wt. % DCP, and 0.16 to 0.18% DMBA residuals exiting the second stage.

Example 3

Conditions were as in example 2 with 1.5 wt. % additional water added ahead of the second stage. An optimal average AMS yield of 82.1% was obtained at 122° C. with 0.02 to 0.04% DCP, and 0.16 to 0.18 wt. % DMBA exiting the second stage.

Example 4

Conditions were as in example 2, but at a 10% higher overall process rate. With no additional water added ahead of a plug flow second stage with 0.7-0.9 minutes of residence time, an average optimal AMS yield of 80.1% was obtained at 108° C., with 0.09 to 0.11 wt. % DCP, and 0.16 to 0.17% DMBA exiting the second stage.

Example 5

Conditions were as in example 4 with 1.5 wt. % additional water added ahead of the second stage. An average optimal AMS yield of 81.0% was obtained at 123° C. with 0.02 to 0.04% DCP, and 0.18 to 0.19 wt. % DMBA exiting the second stage.

Example 6

Conditions were as in example 5, an average optimal AMS yield of 81.6% was obtained at 127° C. with 0.01 to 0.02% DCP, and 0.17 to 0.18 wt. % DMBA exiting the second stage.

Example 7

Conditions were as in example 5 with 1 wt. % additional water added ahead of the second stage. An average optimal AMS yield of 79.6% was obtained at 124° C. with 0.01 to 0.02% DCP, and 0.17 to 0.18 wt. % DMBA exiting the second stage.

Thus and in accordance with the present invention, disclosed is a method for the production of phenol, acetone and alpha-methyl styrene from a mixture of cumene hydroperoxide and dimethylbenzyl alcohol, which comprises a first stage reaction with an acetone to phenol mole ratio of about 1.0-1.5, a water content of about 0.5 to 1.5 wt. %, a sulfuric acid concentration of about 20-400 ppm, a reactor pressure of about 450-760 mm Hg, a temperature of about 60-85° C., and a residence time of 4-45 minutes, with about 0.5 to 3 wt. % additional water then being added prior to a plug flow, and a second stage reactor maintained at about 110-150° C. with a residence time of 0.5 to 30.0 minutes. In a preferred embodiment, the first stage reaction conditions are about 300-350 ppm sulfuric acid, about 450-500 mm Hg operating pressure, about 78-80° C. operating temperature, and a 5-6 minute residence time, the acetone to phenol mole ratio being about 1.25 to 1.35, and the water content being about 1.0-1.2 wt. % in the first stage, and the second stage reaction conditions are a residence time of 0.7 to 1.0 minutes, about 1-2 wt. % additional added water, and a temperature of about 120-140° C.

In a further preferred embodiment of the present invention, exit concentrations of dicumyl peroxide are maintained at about 0.01-0.15 wt. %, the first stage reaction conditions are an acetone to phenol ratio of about 1.0, a sulfuric acid concentration of about 20-50 ppm, atmospheric to slightly negative pressure, and a residence time of 15-45 minutes, and the second stage reaction conditions are a residence time of 5 to 20 minutes, about 1-2 wt. % additional added water, and a temperature of about 120-140° C., with a temperature of 134-138° C. particularly preferred. In another preferred embodiment, exit concentrations of dicumyl peroxide are maintained at about 0.06 to 0.10 wt. %, with about 0.02-0.03 wt. % being particularly preferred.

While the present invention has been described with respect to particular embodiments thereof, it is apparent that numerous other forms and modifications of the invention will be obvious to those skilled in the art. The appended claims and the present invention generally should be construed to cover all such obvious forms and modifications which are within the true spirit and scope of the present invention.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing, all temperatures are set forth uncorrected in degrees Celsius and, all parts and percentages are by weight, unless otherwise indicated.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A method of producing phenol, acetone and alpha-methyl styrene, the method comprising the steps of:
    providing a mixture of cumene hydroperoxide and dimethylbenzyl alcohol;
    subjecting the mixture to a first stage reaction in the presence of about 0.5 to 1.5 wt. % water and about 20 to 400 ppm sulfuric acid at a reactor pressure of about 450 to 760 mm Hg, a temperature of about 60 to 85° C., and a residence time of 4 to 45 minutes to produce a composition having an acetone to phenol mole ratio of about 1 to 1.5; and
    subjecting the composition to a second stage reaction in the presence of about 0.5 to 3 wt. % additional water with a second stage reactor temperature of about 110 to 150° C. and a residence time of 0.5 to 30 minutes.

2. The method of claim 1, wherein the mixture is subjected to the first stage reaction at about 450 to 500 mm Hg operating pressure, about 78 to 80° C. operating temperature, a 5 to 6 minute residence time and in the presence of about 300 to 350 ppm sulfuric acid.

3. The method of claim 2, wherein the mixture has a water content of about 1.0 to 1.2 wt. % while subjecting the mixture to the first stage reaction to produce a composition having an acetone to phenol mole ratio of about 1 to 1.2.

4. The method of claim 1, wherein the composition is subjected to the second stage reaction with a residence time of 0.7 to 1.0 minutes, a temperature of about 120 to 140° C. and with about 1 to 2 wt. % additional water.

5. The method of claim 1, wherein exit concentrations of dicumyl peroxide after the second stage reaction are maintained at about 0.01 to 0.15 wt. %.

6. The method of claim 1, wherein exit concentrations of dicumyl peroxide after the second stage reaction are maintained at about 0.02 to 0.03 wt. %.

7. The method of claim 1, wherein exit concentrations of dicumyl peroxide after the second stage reaction are maintained at about 0.06 to 0.10 wt. %.

8. The method of claim 1, wherein the mixture is subjected to the first stage reaction at atmospheric to slightly negative pressure, a residence time of 15 to 45 minutes and in the presence of about 20 to 50 ppm sulfuric acid to produce a composition having an acetone to phenol ratio of about 1.0.

9. The method of claim 1, wherein the composition is subjected to the second stage reaction with a residence time of 5 to 20 minutes, a temperature of about 120 to 140° C. and about 1 to 2 wt. % additional water.

10. The method of claim 1, wherein the temperature while subjecting the composition to the second stage reaction is about 134 to 138° C.

* * * * *